United States Patent [19]

Dole et al.

[11] Patent Number: 4,847,068

[45] Date of Patent: Jul. 11, 1989

[54] SKIN CARE COMPOSITIONS

[75] Inventors: Victoria F. Dole, Bridgewater, N.J.; Simon D. Monks, Beach Haven, New Zealand; Robert J. Verdicchio, Succasunna, N.J.

[73] Assignee: Johnson & Johnson Consumer Products, Inc., New Brunswick, N.J.

[21] Appl. No.: 82,171

[22] Filed: Aug. 6, 1987

[51] Int. Cl.$^4$ .......................... A61K 47/48; A61K 7/00
[52] U.S. Cl. ..................................... 424/47; 514/772; 514/941; 514/945
[58] Field of Search .................. 424/47; 514/772, 789, 514/844, 846, 847, 873, 939, 941, 945

[56] References Cited

U.S. PATENT DOCUMENTS 3,419,658  12/1968  Sanders ............................ 424/47 X
3,923,970  12/1975  Breuer .................................. 424/47

Primary Examiner—Ellis P. Robinson
Assistant Examiner—Susan S. Rucker
Attorney, Agent, or Firm—Steven P. Berman

[57] ABSTRACT

An aerosol mousse skin care composition comprising mineral oil, an emulsifier, water and a suitable propellant which exhibits desirable foam characteristics, good feel and is non-greasy.

8 Claims, No Drawings

SKIN CARE COMPOSITIONS

BACKGROUND OF THE INVENTION

This invention relates to a skin care product. More particularly, the present invention relates to aerosol mousse skin care products containing mineral oil.

Skin care products such as conditioners and moisturizers are generally available in the form of lotions and creams. Although many such lotions and creams are formulated to be non-greasy, practically all such products are perceived to be somewhat greasy to the touch. In recent years, some attempts have been made to provide such products in aerosol mousse formulations. Often, these have involved no more than making minor modifications of existing skin care lotion formulations and pressurizing them by the addition of propellants. Such lotion formulations traditionally contain relatively high amounts of surfactants, including metallic soap surfactants. Since most of these formulations are emulsions in the lotion format and provide some foam attributes, it is not unexpected that by adding a propellant they will foam when dispensed.

U.S. Pat. No. 4,627,973 discloses skin mousse formulations comprising a combination of at least three skin moisturizers, emollients and/or emulsifiers, namely an alkoxylated methyl glucose derivative, an alkoxylated lanolin derivative and acetylated lanolin alcohol as well as other optional ingredients and a hydrocarbon propellant. U.K. Patent Application No. 2 172 298 A discloses mild skin cleaning mousse formulations containing surfactants, moisturizers and water as well as a propellant. U.S. Pat. Nos. 4,536,390 and 4,567,038 disclose hair products that may be formulated as mousse products. U.S. Pat. No. 3,959,160 discloses aerosol shaving foam compositions which comprise soaps or non-soap anionic surfactants and fatty alcohols and may also contain up to 5% glycerin.

There are currently available in the marketplace various mineral oil products for skin care, conditioning and cleansing. These products normally are non-aqueous formulations containing mineral oil and a fragrance. These products condition and cleanse the skin and impart a smoother feel thereto but when first placed on the skin until rubbed in they are perceived by some consumers to be greasy. Such products are not currently commercially available in mousse formulations.

SUMMARY OF THE INVENTION

It is an object of this invention to provide improved skin care compositions.

It is another object of this invention to provide aerosol mousse skin care compositions.

It is a still further object of this invention to provide aerosol mousse skin care compositions that are non-greasy.

These and other objects and features of the present invention will become readily apparent to one skilled in the art from the detailed description hereinafter.

The foregoing objects and other features and advantages of the present invention are achieved by specific aerosol mousse skin care compositions containing mineral oil.

DETAILED DESCRIPTION OF THE INVENTION

This invention relates to aerosol mousse skin care compositions containing mineral oil. When the term "mousse" is utilized herein, it is intended to cover a product with a pressurized foam delivery system. These compositions provide conditioning and cleansing attributes and a desirable skin feel combined with a rich, creamy foam without the undesirable greasy feel normally associated with mineral oil compositions.

The compositions of the present invention comprise from about 5.0 to 25.0% by weight of the total composition mineral oil; from about 0.5 to 1.5% by weight of the total composition of a nonionic emulsifier; from about 66.5 to 91.5% by weight of the total composition water; and from about 3.0% to 7.0% by weight of the total composition of a suitable propellant. The compositions may also optionally contain small amounts of fragrance and preservatives.

The mineral oil which is useful in the compositions of the present invention is any cosmetically acceptable mineral oil. By "cosmetically acceptable", it is meant any mineral oil that when incorporated into the compositions of the present invention results in suitable skin feel, acceptable foam characteristics and desirable, non-greasy attributes. Mineral oil is a mixture of liquid hydrocarbons obtained from petroleum and may also contain a suitable stabilizer. A suitable mineral oil should also meet USP of NF grade standards. A preferred mineral oil is sold under the tradename Blandol by Witco Chemical, New York, N.Y.

The mineral oil is present in an amount of from about 5.0 to 25.0% by weight of the total composition, preferably about 10.0% by weight. If less than about 5.0% by weight is utilized, the resulting compositions will not have the desired conditioning, cleansing and feel characteristics and if greater than about 25.0% by weight is utilized, the resulting compositions may exhibit poor foam characteristics and may also be perceived as greasy. It is believed that these characteristics can be controlled by adjusting the other components of the composition and therefore amounts of mineral oil greater than about 25% may be satisfactory in some compositions.

The nonionic emulsifiers which are useful in the compositions of the present invention are specific ethoxylated fatty alcohols, i.e., those having a saturated hydrocarbon chain length of $C_{16}$ to $C_{18}$ and a suitable polyoxyethylene chain length, i.e., less than 10. Specific ethoxylated fatty alcohols include polyoxyethylene (2) stearyl ether sold under the tradename Brij 72 by ICI Americas, Wilmington, Del. and polyoxyethylene (2) cetyl ether sold under the tradename Brij 52 by ICI Americas, Wilmington, Del. It is also possible to utilize mixtures of ethoxylated fatty alcohols including ethoxylated fatty alcohols that are not useful alone. Furthermore, it is possible to utilize mixtures of ethoxylated fatty alcohols and phosphate esters such as those available under the tradename Crodaphos SG from Croda, Inc., New York, N.Y., mixtures of ethoxylated fatty alcohols with mixtures of fatty alcohols and ethoxylated sorbitan esters such as those available under the tradename Polawax A31 from Croda, Inc., New York, N.Y. and mixtures of ethoxylated fatty alcohols with silicone surfactants such as those available under the tradename Dow Corning 193 Silicone Surfactant from Dow Corning Corp., Midland, Mich.

The emulsifier is present in an amount of from about 0.5 to 1.5% by weight of the total composition, preferably about 1.0 to 1.2%. If less than about 0.5% by weight is utilized, the resulting compositions will not form satisfactory emulsions and little or no foam will be generated. If greater than about 2.0% by weight is utilized, the resulting compositions may lose some of their desirable non-greasy attributes and the conditioning benefits of the mineral oil could be decreased.

It is surprising that such a relatively small amount of emulsifier can produce an effective foam. This is even more surprising since it is well-known that mineral oil acts as a defoamer and is known to be difficult to emulsify. Mineral oil lotion compositions require large amounts of emulsifiers to obtain a useful emulsion due to these characteristics of mineral oil. While applicants do not wish to be bound by the following explanation, it is believed that the specific compositions of the present invention have the necessary surface properties to provide a basis for a stable interfacial film between the air, liquid and solid phases resulting in a stable mousse product.

Water is present in the compositions of the present invention in an amount of from about 66.5 to 91.0% by weight of the total composition.

The compositions of the present invention may optionally contain small amounts of a preservative such as Dowicil 200, Dow Chemical Company's tradename for the cis isomer of 1-(3-chloroalkyl)-3,5,7-triaza-1-azoniaadamantine chloride and Kathon CG, Rohm & Haas' tradename for methyl- and methylchloro- isothiazolinones and from about 0.05% to 0.25% by weight of a suitable fragrance.

It has further been found that the selection of a specific propellant is important to obtain the desired characteristics in the compositions of the present invention. Not all the propellants normally utilized in such compositions are useful in the present invention. For example, hydrocarbons and hydrocarbon mixtures such as butane, isobutane and propane are not particularly useful, i.e., produce a less satisfactory foam, and furthermore these propellants result in flammable formulations. Propellants which are useful in the present invention include fluorinated hydrocarbons such as 1,1-difluoroethane, 1-chloro-1, 1-difluoroethane, chlorodifluoromethane and mixtures thereof. These propellants are available under the Dymel tradename from E. I. DuPont de Nemours, Wilmington, Del. Other propellants which are useful are the halogenated hydrocarbons available under the Freon tradename from DuPont. These propellants result in the compositions exhibiting good foam characteristics, and furthermore the resulting formulations are not flammable. It is also possible to use mixtures of these propellants with known hydrocarbon propellants which may not be useful alone. The propellants should be utilized in an amount from about 3.0% to 7.0% by weight of the total composition preferably about 3.5% to 4.5%.

The compositions of the present invention can be prepared by first dissolving the emulsifier into the mineral oil followed by the addition of this mixture into deionized water to form an emulsion. The emulsions are then pressurized with a suitable propellant according to conventional means and utilizing conventional packaging.

Specific embodiments of the compositions prepared in accordance with the present invention are illustrated by the following representative examples. It will be understood, however, that the invention is not confined to the specific limitations set forth in the individual examples, but rather to the scope of the appended claims.

EXAMPLE I

A mousse skin care composition is prepared as follows: In a suitable vessel are combined 100 grams of light mineral oil (Mineral Oil, NF) and 12 grams of Brij 72 (polyoxyethylene (2) stearyl ether). The mixture is stirred and heated to 50° C. to provide a clear solution. In a separate vessel 886.0 grams of water are heated to 50° C. The mineral oil-emulsifier solution is then stirred into the water to form an emulsion. The emulsion is cooled and a preservative (Kathon CG, 0.5 g) and fragrance (1.5 grams) are added. The resulting emulsion product is mixed until uniform.

The emulsion is filled into a suitable aerosol package of conventional type together with the propellant (1,1-difluoroethane) in the proportion of 96.5 parts of the above emulsion to 3.5 parts of propellant. The package is completed by attachment of a suitable dispensing valve and actuator to form the finished product.

The product has the following formulation:

|  | % wt/wt |
| --- | --- |
| mineral oil | 9.65 |
| polyoxyethylene (2) stearyl ether (sold under the tradename Brij 72 by ICI Americas) | 1.16 |
| Kathon CG | 0.05 |
| fragrance | 0.14 |
| propellant | 3.50 |
| deionized water | q.s. to 100.00 |

The resulting product can be tested for foam quality by inspection and by a standard test method. It can also tested for use characteristics by individual and panel methods of application and evaluation.

The visual inspection for foam quality is an examination for a desirable "creamy" texture and appearance comprising uniform, small bubble formation, foam stability on dispensing and suitable spreading on the skin. The proper foam consistency is judged by dispensing a small quantity of mousse foam on a flat solid substrate, which is then inclined to a near-vertical orientation. The minimum criterion for foam quality is that the dispersed foam does not run down the inclined surface over a period of one minute.

Use characteristics are evaluated by methods involving controlled application to simulate product use, followed by individual rating and assessment of such factors as spreading, quick-breaking of the mousse foam, greasiness, tackiness and speed of rub-in, as well as accessory characteristics such as fragrance preferences.

The standard test method for foam density involves dispensing the mousse foam from a composition previously stabilized at standard temperature, into a standard volumetric cone. The empty cone is weighed and the cone is then filled with water and weighed to determine the volume of the cone. The clean empty cone is then tared and the mousse foam is dispensed through a small orifice at the small end of the cone in such a manner as to completely and uniformly fill the cone. Excess foam is removed from the large end opening of the cone by use of a straight-edge tool, and the filled cone is weighed. The foam density is then determined as a ratio of the weight of the mousse foam filling the cone divided by the volume of the cone previously determined.

The product of Example I gives a desirable foam upon visual examination and exhibits a satisfactory foam density when tested according to the above procedure.

EXAMPLE II

A mousse skin care composition is prepared according to the procedure of Example I and has the following formulation:

|  | % wt/wt |
| --- | --- |
| mineral oil | 9.65 |
| Brij 72 | 1.16 |
| Kathon CG | 0.05 |
| fragrance | 0.14 |
| propellant (1,1-difluoroethane) | 3.00 |
| deionized water | q.s. to 100 |

When tested according to the procedure of Example I, this composition exhibits desirable foam quality and the resulting composition is not flammable according to ASTM Tag Open-Cup Test Procedure D1310-85.

When the propellant of the above composition is replaced by a hydrocarbon propellant comprising a 20/80 mixture of propane and isobutane, the foam quality and density is not as desirable, and furthermore the resulting composition is flammable.

EXAMPLE III

A mousse skin care composition is prepared according to the procedure of Example I and has the following composition:

|  | % wt/wt |
| --- | --- |
| mineral oil | 9.50 |
| Brij 72 | 1.14 |
| Kathon CG | 0.05 |
| fragrance | 0.15 |
| propellant (1,1-difluoroethane) | 5.00 |
| deionized water | q.s. to 100 |

When tested according to the procedure of Example I, the composition has satisfactory foam quality, although of a drier texture, and thus with less satisfactory spreading characteristics than the foam resulting from the composition of Example II.

EXAMPLE IV

A mousse skin care composition is prepared according to the procedure of Example I and has the following composition:

|  | % wt/wt |
| --- | --- |
| mineral oil | 9.65 |
| Brij 72 | 0.47 |
| Kathon CG | 0.05 |
| fragrance | 0.15 |
| propellant (1,1-difluoroethane) | 3.5 |
| deionized water | q.s. to 100 |

When tested according to the procedure of Example I, the composition has satisfactory foam quality, although the dispensing texture and flow characteristics are those of a thinner, runnier foam with a shorter break time.

EXAMPLE V

A mousse skin care composition is prepared according to the procedure of Example I and has the following composition:

|  | % wt/wt |
| --- | --- |
| mineral oil | 19.30 |
| Brij 72 | 1.54 |
| Kathon CG | 0.05 |
| fragrance | 0.20 |
| Propellant (1,1-difluoroethane) | 3.50 |
| deionized water | q.s. to 100 |

When tested according to the procedure of Example I, this composition exhibits a desirable, creamy foam quality.

When examined for use characteristics, this composition is found to be satisfactory, with a satisfactory rub-in characteristics and a substantial protective feeling without greasiness.

EXAMPLE VI

A mousse skin care composition is prepared according to the procedure of Example I and has the following composition:

|  | % wt/wt |
| --- | --- |
| mineral oil | 9.65 |
| polyoxyethylene (4) lauryl ether (Brij 30) | 1.16 |
| Kathon CG | 0.05 |
| fragrance | 0.15 |
| propellant (1,1-difluoroethane) | 3.50 |
| deionized water | q.s. to 100 |

When tested according to the procedure of Example I, this composition exhibits unsatisfactory foam quality. The mousse foam is of thin and runny consistency, with irregular bubble size and excessively quick breaking character.

EXAMPLE VII

A mousse skin care composition concentrate is prepared according to the procedure for preparing the emulsion part of Example I and has the following composition:

|  | % wt/wt |
| --- | --- |
| mineral oil | 10.00 |
| polyoxyethylene (2) oleyl ether (Brij 93) | 1.20 |
| Kathon CG | 0.05 |
| fragrance | 0.15 |
| deionized water | q.s. to 100 |

When examined for suitable emulsion characteristics, the composition is found to be unsatisfactory for use in aerosol mousse applications. It has a poor emulsion uniformity, with poor stability of the emulsion form, that is, it exhibits separation of the oil and water phases in a short period of time and is not suitable for use in an aerosol composition.

EXAMPLE VIII

A mouse skin care composition is prepared according to the procedure of Example I and has the following composition:

|  | % wt/wt |
| --- | --- |
| mineral oil | 9.65 |
| Brij 72 | 0.78 |
| Brij 30 | 0.39 |
| Kathon CG | 0.05 |
| fragrance | 0.15 |
| propellant (1,1-difluoroethane) | 3.50 |
| deionized water | q.s. to 100 |

When examined according to the procedure of Example I, the composition is found to have desirable mousse foam characteristics, with uniform small bubble size, good spreading characteristics and good foam stability.

EXAMPLE IX

A mousse skin care composition is prepared according to the procedure of Example I and has the following composition:

|  | % wt/wt |
| --- | --- |
| mineral oil | 9.65 |
| Brij 72 | 0.68 |
| Polawax A31 (a cetearyl alcohol sorbitan ester composition sold by Croda, Inc.; falling within the scope of the NF description of "Emulsifying wax, NF") | 0.48 |
| Kathon CG | 0.05 |
| fragrance | 0.15 |
| propellant (1,1-difluoroethane) | 3.50 |
| deionized water | q.s. to 100 |

When examined according to the procedure of Example I, the composition is found to have desirable mousse foam characteristics, uniform small bubble size, good spreading characteristics and good foam stability. In use, the product give a smooth, non-tacky, non-greasy feel on the skin.

EXAMPLE X

A mousse skin care composition is prepared according to the procedure of Example I and has the following composition:

|  | % wt/wt |
| --- | --- |
| mineral oil | 9.65 |
| Brij 72 | 0.97 |
| Crodaphos SG | 0.20 |
| Kathon CG | 0.05 |
| fragrance | 0.15 |
| propellant (1,1-difluoroethane) | 3.50 |
| deionized water | q.s. to 100 |

When examined according to the procedure of Example I, the composition is found to have desirable mousse foam characteristics, uniform small bubble size, good spreading characteristics and good foam stability. In use, the product provides a smooth, non-tacky, non-greasy feel on the skin.

EXAMPLE XI

A mousse skin care composition is prepared according to the procedure of Example I and has the following composition:

|  | % wt/wt |
| --- | --- |
| mineral oil | 9.65 |
| Brij 72 | 0.97 |
| silicone surfactant (sold under the tradename Dow Corning 193 silicone surfactant by Dow Corning Corp.) | 0.20 |
| Kathon CG | 0.05 |
| fragrance | 0.15 |
| propellant (1,1-difluoroethane) | 3.50 |
| deionized water | q.s. to 100 |

When examined according to the procedure of Example I, the composition is found to have desirable mousse foam characteristics, uniform small bubble size, good spreading characteristics and good foam stability. In use, the product provides a smooth, non-tacky, non-greasy feel on the skin.

In addition to the preferred embodiments described herein, other embodiments, arrangements and variations within the spirit of the invention and the scope of the appended claims will occur to those skilled in the art.

What is claimed is:

1. A skin care composition to be dispensed from a pressurized aerosol container comprising:
   (a) from about 5.0 to 25.0% by weight of the total composition mineral oil;
   (b) from about 0.5 to 1.5% by weight of the total composition of an emulsifier selected from the group consisting of ethoxylated fatty alcohols having a saturated hydrocarbon chain length of 16 to 18 and a polyoxyethylene chain length of less than 10 and mixtures of said ethoxylated fatty alcohols with other ethoxylated fatty alcohols, mixtures of fatty alcohols and ethoxylated sorbitan esters, phosphate esters or silicone surfactants;
   (c) from about 3.0 to 7.0% by weight of the total composition of a propellant selected from the group consisting of fluorinated hydrocarbons, chloro-fluorinated hydrocarbons and mixtures of hydrocarbons and fluorinated hydrocarbons or chloro-fluorinated hydrocarbons; and
   (d) the balance water.

2. The skin care composition of claim 1 wherein the emulsifier is polyoxyethylene (2) stearyl ether.

3. The skin care composition of claim 1 wherein the emulsifier is polyoxyethylene (2) cetyl ether.

4. The skin care composition of claim 1 wherein the propellant is a fluorinated hydrocarbon.

5. The skin care composition of claim 1 wherein the propellant is 1,1-difluoroethane.

6. The skin care composition of claim 1 containing about 10% by weight of the total composition of mineral oil.

7. The skin care composition of claim 1 containing about 1.0 to 1.2% by weight of the total composition of the emulsifier.

8. The skin care composition of claim 1 containing about 3.5 to 4.5% by weight of the total composition of the propellant.

* * * * *